United States Patent [19]

Westman

[11] 4,129,415

[45] Dec. 12, 1978

[54] METHOD FOR REMOVING PERMANENT DYES FROM HAIR AND OTHER KERATINACEOUS MATERIALS

[75] Inventor: Morton A. Westman, Fort Lee, N.J.

[73] Assignee: American Cyanamid Company, Stamford, Conn.

[21] Appl. No.: 870,303

[22] Filed: Jan. 18, 1978

Related U.S. Application Data

[63] Continuation of Ser. No. 732,618, Oct. 15, 1976, abandoned.

[51] Int. Cl.$^2$ .............................................. D06L 3/00
[52] U.S. Cl. ........................................ 8/102; 8/127.6; 132/7; 252/105; 424/62
[58] Field of Search ........ 8/102, 109, 127.6, DIG. 11; 132/7, DIG. 4; 424/62, DIG. 3; 252/105

[56] References Cited

U.S. PATENT DOCUMENTS

| 3,144,300 | 8/1964 | Cosnard et al. | 8/127.6 |
| 3,397,942 | 8/1968 | Renault | 8/127.6 |
| 3,397,943 | 8/1968 | Renault | 8/127.6 |
| 3,423,164 | 1/1969 | Trezain | 8/127.6 |
| 3,423,165 | 1/1969 | Trezain | 8/127.6 |
| 3,528,921 | 9/1970 | Gray | 252/105 |
| 3,706,670 | 12/1972 | Gray | 252/105 |
| 3,954,652 | 5/1976 | Schmidt | 252/105 |

*Primary Examiner*—William E. Schulz
*Attorney, Agent, or Firm*—Charles J. Fickey

[57] ABSTRACT

A method for removing permanent oxidation-type dyes from human hair and other keratinaceous materials, and more particularly to the use of dichloroisocyanuric acid and sodium bisulfite to remove permanent dyes from hair by a two-step procedure.

4 Claims, No Drawings

METHOD FOR REMOVING PERMANENT DYES FROM HAIR AND OTHER KERATINACEOUS MATERIALS

This a continuation of application Ser. No. 732,618 filed Oct. 15, 1976, and now abandoned.

The present invention relates to a method for removing permanent oxidation-type dyes from human hair and other keratinaceous materials, and more particularly to the use of dichloroisocyanuric acid and sodium bisulfite to remove permanent dyes from hair by a two-step procedure.

Hair coloring and bleaching preparations in various forms have been used extensively for years. Today, dyes for hair can be classified as temporary, semi-permanent and permanent. The latter are the most important, since they last until the hair grows out. These dyes can give very deep dyeings and are generally fast to commercial shampoo formulations. Although the permanent type dyes have many advantages, they are very difficult to remove from the hair once they have been applied. Thus, if for any reason the wearer is dissatisfied, the dye can only be removed with considerable difficulty, often accompanied by damage to the hair. Bleaching is sometimes used, and weak solutions of sodium hydrosulfite or sodium thiosulfate have also been used for removal of the dyes.

In view of the present difficulty in removing permanent dyes from hair and other keratinaceous materials, there is a need for an effective, relatively simple method for removing them.

I have now discovered that permanent oxidation-type dyes can be readily removed from hair and other keratinaceous material, without damaging the hair, by the application thereto of weak solutions of dichloroisocyanuric acid and sodium bisulfite. Surprisingly, I have also discovered that the method of this invention, rather than damaging the hair, actually improves the properties of hair associated with "conditioning", i.e. ease of wet combability, reduction of flyaway, body, and the like.

Oxidation type dyes and dye processed are well-known. The process is unique in that washfast pigments are formed in situ in the hair. In the process, alkaline solutions of dye intermediates are mixed with an oxidizing agent just before application to the hair. When the mixture is applied, the alkali swells the hair, allowing the dye intermediates to penetrate. There they are oxidized to form washfast pigments.

Oxidation dye intermediates are analogs or derivatives of p-phenylene diamine, aromatic amines, aromatic diamines, aromatic phenols, and the like.

They are applied from a dye base which is an aqueous solution of soap or synthetic detergent which provides the wetting, spreading and penetration required. Ammonia is normally used to adjust the pH to 9–10, and provide swelling of the hair. The dye base contains a dye developer or oxidizing agent, incorporated just prior to application to the hair. Usually this is hydrogen peroxide.

The procedure for removing the above-described oxidation dyes from hair or other keratinaceous materials in accordance with the present invention involves two steps. The first step is to treat the dyed hair with a weak solution of dichloroisocyanuric acid. Dichloroisocyanuric acid, i.e. dichloro-s-triazine-2,4,6-trione, is a well-known compound which is used in household dry bleaches, dishwashing compounds, scouring powders, and the like. A dilute solution containing about from 0.5 to 7 percent, preferably 1 to 4 percent, dichloroisocyanuric acid in water is buffered to a pH of about 4 to 7, preferably about 7. This dilute solution is applied to the dyed hair. The solution is left on the hair for a period of time sufficient to remove the dye, usually ranging from about 5 to 20 minutes, and then rinsed to remove the solution. The rinsed hair is then treated with a weak aqueous solution of sodium bisulfite. This solution will contain about 0.5 to 7 percent sodium bisulfite, preferably about 1 to 4 percent. The solution is left on the hair for a period of time sufficient to complete dye removal, usually about 5 to 20 minutes, and then thoroughly rinsed off with warm water.

When the dyed hair is treated as described above, the dye is essentially completely removed from the hair. There is no evidence of hair damage, and the hair is actually left in good condition.

Although the invention has been described in terms of removing permanent oxidation type dyes from human hair, it is also applicable to removing permanent dyes from other keratinaceous materials, such as animal fur, bristles, feather, wool, and the like.

The following example further illustrates the method of the invention.

EXAMPLE

A small piece of previously dyed virgin white hair was treated with a solution of 3.0 percent dichloroisocyanuric acid, buffered to pH 7 with sodium phosphate buffers. The solution was left on the hair for about 15 minutes and then rinsed off. The hair was then treated with a solution of 3.0 percent sodium bisulfite in water, the solution left on the hair for about 5 minutes, and the hair then thoroughly rinsed with warm water. The dye had been essentially removed from the hair.

I claim:

1. A method for the removal of permanent oxidation-type dyes from hair and other keratinaceous materials which comprises treating said dyed hair with a dilute solution of dichloro-s-triazine-2,4,6-trione for a period of about 5 to 20 minutes; rinsing said solution from the hair with water; treating the hair with a dilute solution of sodium bisulfite for a period of about 5 to 20 minutes; and thoroughly rinsing said treated hair with water.

2. The method according to claim 1 wherein the hair or other keratinaceous material is first treated with a solution containing from about 0.5 to 7 percent dichloro-s-triazine-2,4,6-trione.

3. The method according to claim 1 wherein the hair or other keratinaceous material is treated with a solution containing from about 0.5 to 7 percent sodium bisulfite.

4. The method according to claim 1 wherein said solution of dichloro-s-triazine-2,4,6-trione is buffered to pH 4–7.

* * * * *